United States Patent [19]

Bullock

[11] 4,180,911

[45] Jan. 1, 1980

[54] METHOD FOR DIRECT BONDING OF ORTHODONTIC STRUCTURES TO TEETH USING FLOURIDE PRETREATMENT

[75] Inventor: Richard S. Bullock, Chicago, Ill.

[73] Assignee: Applied Science Corporation, Chicago, Ill.

[21] Appl. No.: 833,717

[22] Filed: Sep. 16, 1977

[51] Int. Cl.² ............................ A61C 7/00; C09K 3/00
[52] U.S. Cl. .......................................... 433/9; 106/35; 433/228
[58] Field of Search ............... 128/260; 32/15, 14 R, 32/14 C, 14 A, 66; 424/49, 52; 260/42.14, 42.15; 401/1, 2; 156/276, 295; 106/35

[56] References Cited

U.S. PATENT DOCUMENTS

| | | | |
|---|---|---|---|
| 3,066,112 | 11/1962 | Bowen | 32/15 |
| 3,250,002 | 5/1966 | Collito | 32/15 |
| 3,259,534 | 7/1966 | Wicker, Jr. et al. | 156/331 |
| 3,452,436 | 7/1969 | Woskin | 32/14 A |
| 3,485,417 | 12/1969 | Cocks | 401/1 X |
| 3,518,762 | 7/1970 | Takeuchi | 32/15 |
| 3,688,406 | 9/1972 | Porter | 128/260 |
| 3,862,920 | 1/1975 | Foster et al. | 106/35 |
| 3,969,499 | 7/1976 | Lee, Jr. et al. | 32/15 |

Primary Examiner—Louis G. Mancene
Assistant Examiner—Michael J. Foycik
Attorney, Agent, or Firm—Gerald T. Shekleton

[57] ABSTRACT

A method and composition for the use of a cyanoacrylate resin and a silane-treated inorganic powder in direct bonding mount/bracket structures to teeth and other dental applications. The method and composition inhibit caries formation about the tooth structure interface and the adhesive is easily removed.

15 Claims, 4 Drawing Figures

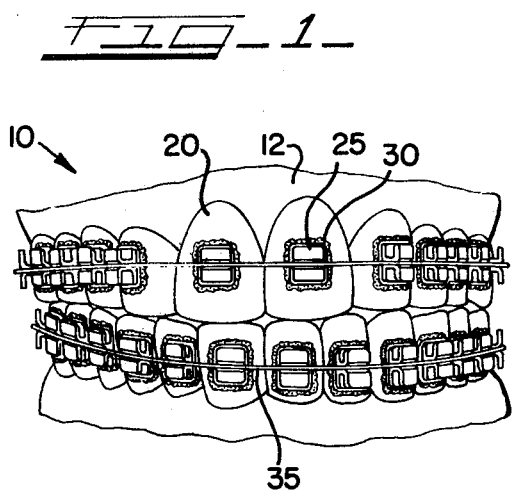
FIG_1_
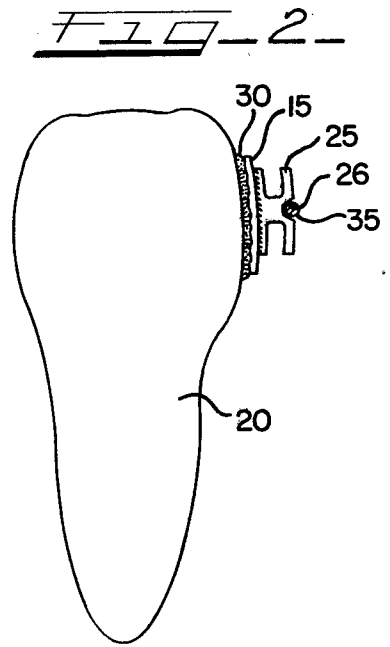
FIG_2_
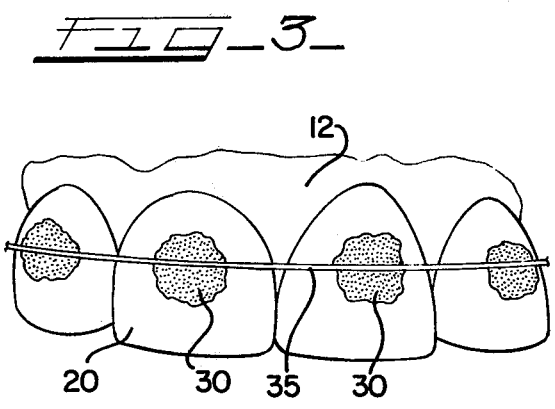
FIG_3_
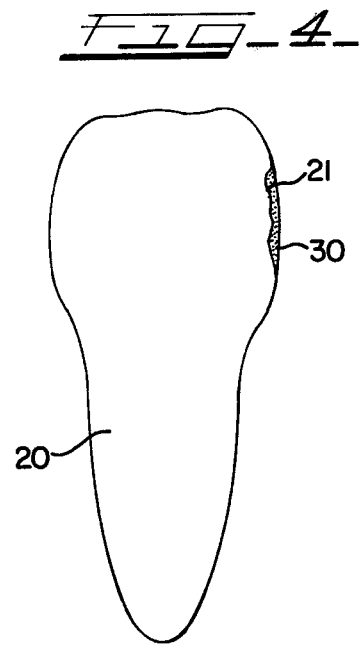
FIG_4_

METHOD FOR DIRECT BONDING OF ORTHODONTIC STRUCTURES TO TEETH USING FLOURIDE PRETREATMENT

This application relates to orthodontic dentistry, and more particularly, relates to the direct bonding of orthodontic brackets to teeth.

BACKGROUND OF THE INVENTION

In the past, the generally accepted manner of orthodontically bracketing teeth involved the use of metal bands encircling the teeth involved in the treatment. These bands are held in place with cement. These bands are generally of stainless steel which were preformed to fit the size and contour of the particular tooth. The tooth to band interface is filled with common dental cement, such as zinc oxide cement, to aid in keeping the band and bracket structure secured about the tooth in a prescribed position and to prevent food from lodging in the interface. However, the zinc oxide cement as well as other cements in use were generally acidic; therefore long exposure of tooth enamel to the cement would often cause demineralization of the contact tooth surface. Not only were these demineralized areas unattractive, but they were also more vulnerable to caries development. A particular difficulty encountered with the use of these bands was the protection of the tooth from caries development as a result of the above-mentioned acidic cement and the necessity for constant cleaning or brushing of the teeth to dislodge food particles and the like.

As a result of the above-described disadvantages of the band and bracket orthodontic system, interest has developed of late in the development of a bandless system which has become popularly known as a direct bond orthodontic system. Such a direct bonding system is advantageous to the practice of orthodontistry as it can reduce chair time and the treatment period. The patient benefits as a minimum of dental area is occupied by the direct bonding system, thereby greatly improving the aesthetics of the orthodontic treatment. However, limitations have been placed on the use of the direct bonding orthodontic system. Present practices dictate the necessity for treating the tooth surface by etching with a phosphoric acid solution in an effort to prepare the tooth surface for allowing the proper interface between the adhesive and the tooth. Generally, the phosphoric acid must be in contact with the tooth surface for a period of 30–60 seconds for proper etching of the tooth surface to occur. The strength and nature of the phosphoric acid solution used dictates that any contact of the gingivae or gums with the acid solution be avoided and that if contact should occur, the area should be flushed with copious amounts of water.

Other problems occurring with acid-etched base bonding systems present themselves when removing the orthodontic apparatus from the teeth. Permanent damage to the tooth can occur in either of two major ways, most predominantly involving fracture of the tooth surface itself when the orthodontic apparatus is removed from the tooth. Another type of damage can occur when some adhesive residue remains on the tooth and cannot be removed completely. In such occurrences, the orthodontist must grind the residue away, re-exposing the original tooth surface where no acid-etching occurred. However, where the tooth surface was originally acid-etched, the adhesive residue will lodge in the interstices of the etched surface and may only be smoothed over and not removed. Thus, there will be a permanent alteration of the tooth surfaces that were etched. The adhesive residue thus left on the tooth surface may be microscopic when viewed individually, but collectively the residue area can be noticeable and not aesthetically pleasing.

SUMMARY OF THE INVENTION

Thus, an object of the composition and method of the subject invention is an orthodontic system for direct bonding mounts and brackets to tooth surfaces without the necessity to acid-etch the tooth surface.

Another object of the subject invention is the use of a unique resin which makes possible the direct bonding of the orthodontic apparatus to the tooth surfaces without the necessity of acid-etching the tooth.

A still further object of the subject invention is the use of a resin which is easily and safely removed from the tooth surface upon removal of the orthodontic apparatus from the mouth.

A still further object of the subject invention is a method and composition for direct bonding orthodontic apparatus to tooth surfaces while subsequently protecting the interface between the orthodontic apparatus and the tooth surface from caries.

A still further object of the method and composition of the subject invention is its use as a pit and fissure sealant and overall dental restorative.

These and other objects are obtained in accordance with the present invention wherein there is provided a method and composition for bonding orthodontic apparatus to human tooth surfaces and for the repair, restoration, and sealing of human teeth in dental procedures. The conventional sequence used by an orthodontist in placing orthodontic mount and bracket structures onto a tooth may be used in the method and composition of the subject invention including the steps of preparation of the tooth surface, mixing the adhesive, fixing the mount and bracket structure, and curing the adhesive. With the subject invention, preparation of the tooth surface allows a normal cleaning of the teeth in the brushing of the teeth by the patient at home. The tooth surface is blotted dry and a stannous flouride solution is applied to the dried surface. The adhesive, a cyanoacrylate, is mixed with a filler, preferably a silica powder, although other fillers may be used. If desired, the color of the adhesive may be altered to match the variable colors of the tooth surfaces by the addition of standard inorganic colorants such as titanium dioxide. The adhesive is placed on the surface of the mount/bracket structure which will be in contact with the tooth and immediately placed on the treated tooth surface. The mount/bracket structure is held in place until the adhesive has completely cured. Curing may be accelerated by the application of heat to either the mount/bracket and/or interface area. The use of the stannous fluoride pretreatment and the impervious and stable nature of the cyanoacrylate adhesive reduces the possibility of caries development in the area around and underneath the bracket mount during the treatment period. In addition, the stannous fluoride pretreatment makes possible a strong, lasting bond to the tooth surface.

The mount/bracket structures may be easily removed and the tooth surfaces restored to their original state by the use of a fast and uncomplicated procedure. The application of a dimethylformamide solution to the periphery of the interface between the tooth and the mount/bracket structure will dissolve the resin by solvation and release the mount/bracket structure from the tooth. Continued swabbing of the tooth with the solvent in moderate amounts will remove the final remnants of the adhesive.

The use of the method and composition of the subject invention is ideally suited for use as a dental restorative or the filling of newly-exposed surfaces of the tooth with the inventive composition after the pretreatment with stannous fluoride. In addition, the subject method and composition may be used for securing dental crowns and bridgework in desired positions as well as sealing pits and fissures on human tooth surfaces.

DESCRIPTION OF THE DRAWINGS

Further object of the invention together with additional features contributing thereto and advantages accruing therefrom will be apparent from the following description of one embodiment of the invention when read in conjunction with the accompanying drawings wherein:

FIG. 1 is a perspective view showing a conventional direct bonded orthodontic mount/bracket structure on teeth;

FIG. 2 is a side view showing a mount/bracket structure and interface with the tooth surface;

FIG. 3 is a perspective view showing direct bonding of an arch wire directly to the tooth surface; and, FIG. 4 is a side view of a tooth showing the use of the method and composition of the subject invention as a dental restorative.

Referring now to FIG. 1, there is shown a mouth interior comprising teeth 20, gingivae or gums 12. When teeth grow misshapen or otherwise not in alignment with one another inside the mouth, the orthodontist may prescribe the use of an orthodontic mouth/bracket apparatus as a means of straightening out the teeth in the moutn and relative to one another. As stated above, recent advances in orthodontics have yielded the direct bonding technique of placing mount/bracket structures to the surface. As shown in FIGS. 1 and 2, the mount 25 is bonded to the tooth surface 20 by means of an adhesive 30. The adhesive 30 provides the interface between the tooth surface and the mount and must be of such a strength as to withstand the severe strains placed on the teeth during the chewing and eating function. On the mount 15 is secured a bracket 25. Arch wire 35 is fixed and secured within a recess 26 of the bracket, thereby placing stress on the tooth for forcing it to a desired position. The advantages of the direct bonding mount/bracket system include improved aesthetics over the traditional banding procedure whereby the brackets are mounted on a band which encircles the tooth, thereby providing a large amount of interfacial contact between the band and the tooth in which caries may develop. In addition, the direct bonding technique provides for simplified orthodontic procedure and reduced chair time. However, as mentioned above, one of the drawbacks of the direct bonding technique is its use of an etching agent, generally phosphoric acid, in the mouth area. While such use is accepted dental practice, it does present undesirable risks.

By the method of the subject invention, the use of a strong etching agent is unnecessary and pretreatment is accomplished by first drying the tooth surface with a cotton roll or like material, then applying a 6-8% solution of stannous fluoride ($SnF_2$) in water to the dried tooth surface, letting the solution remain on the tooth for up to two minutes. At the end of this period, the tooth is rinsed with copious amounts of water to remove the excess stannous fluoride solution. This application of stannous fluoride is believed to provide two functions in the pretreatment of the tooth surface. The tooth is protected from the development of caries on the treated area which will be covered by the mount/bracket structure. The well-documented effect of stannous fluoride in the protection of the tooth from caries supports this belief. The stannous fluoride treatment, more importantly, also appears to act as a bridging means between the tooth surface and the adhesive to enhance the bond strength under water or in the oral environment. With such a pretreatment there is no real physical alteration of the tooth surface as in the acid-etching procedure and no extraordinary precautions need be taken, as stannous fluoride is conventionally used in the normal prophylactic cleaning of the teeth. The bridging means then can strengthen the bond and allows the adhesive of the subject invention to be applied without the necessity of an absolutely dry tooth surface, as in the use of prior art adhesives.

After the preparation of the tooth surface, the adhesive is mixed. The adhesive 30 comprises two basic constituents, a resin and a filler. The resin material of choice is a cyanoacrylate resin which is of low viscosity. It becomes desirable to increase the viscosity of the resin so there is no runoff or dripping and a controlled cure can be realized when applied to the mount and placed on the tooth surface. Thus, the cyanoacrylate is mixed with a filler such as a silane treated silica powder. This treated silica is hydrophobic, and therefore increases the resistance of the adhesive to the water or other aspects found in the oral environment. The color of the adhesive mix may be adjusted with any of the commercial dental inorganic colorants or whitening agents accepted for dental use, including powdered, silane treated titanium dioxide.

Preferably, the cyanoacrylate resin used is ethyl cyanoacrylate; however, any liquid ester cyanoacrylate having the general structure:

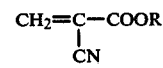

where R is a hydrocarbon having a chain length of 1-12 carbon atoms and preferably of 1-4 carbon atoms. Of course, the hydrocarbon may be any substituted hydrocarbon, such as a fluorinated hydrocarbon. The liquid resin may be a mixture of monomer and polymer or prepolymer, dependent on the actual viscosity and flow properties desired.

The filler, as stated above, may have a base of any inorganic or ceramic powder such as calcium carbonate, aluminum silicates, magnesium silicates, alumina, or various clays such as Kaolinite, Bentonite, and Montmorillonite. Any of these filler base materials, when treated with a silane or combination of silanes will become hydrophobic and provide good results in the application and curing of the adhesive to the surface. The silanes with which the filler material may be treated include:

Vinyl-tris (beta-methoxyethoxy) silane (Silane A)
  gamma-Methacryloxypropyltrimethoxysilane (Silane B) beta-(3,4-Epoxycyclohexyl) ethyltrimethoxysilane (Silane C)
  gamma-Gylcidoxypropyltrimethoxysilane (Silane D)

gamma-Mercaptopropyltrimethoxysilane (Silane E)
gamma-Aminopropyltriethoxysilane (Silane F)
N-beta-(aminoethyl)-gamma-Aminopropyltriethoxysilane (Silane G) and
Styryl amine functional silane (Silane H)
(Silane H has the structure of

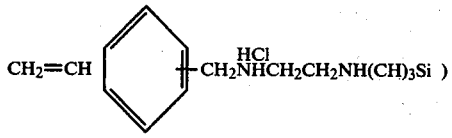

For convenience and ease of understanding, the above-identified silanes will be referred to by Silane A, Silane B, etc.

The silane treated fillers may be used alone or in combinations in various ratios. The following combinations of silane treated fillers have been tried and found to have beneficial properties:

| Mixture I | Mixture II |
|---|---|
| 60% Silane D treated filler | 50% Silane F treated filler |
| 40% Silane H treated filler | 50% Silane D treated filler |
| Mixture III | Mixture IV |
| 50% Silane F treated filler | 40% Silane D treated filler |
| 50% Silane B treated filler | 40% Silane H treated filler |
|  | 20% Silane B treated filler |
| Mixture V | |
| 30% Silane F treated filler | |
| 30% Silane H treated filler | |
| 40% Silane B treated filler | |

For optimum results, the filler should have a particle size of 50 microns or less.

The properties of the adhesive will vary dependent on the filler base or combination of filler bases used, its particle size and the silane with which it is treated. Curing and flow characteristics of the adhesive are dependent on the choice of the actual properties of filler used.

The adhesive may be mixed by placing a small quantity of the treated silica onto an appropriate mixing surface and adding the cyanoacrylate liquid to the liquid and mixing until a desired consistency is reached, taking care to completely mix the two components until there is uniform consistency throughout.

The adhesive prepared, as described above, can be placed onto the surface of the mount which will be placed against the tooth surface by either dipping the mount portion into the bonding material mixture or placing a small quantity of the bonding material mixture onto the mount surface with the mixing spatula. The mount/bracket structure is then immediately placed upon the pretreated tooth surface and held in place until a complete cure of the adhesive is effected. The room temperature curing time of the adhesive can be varied by the selection of the particular cyanoacrylate resin used, the filler material and the various possible ratios of resin to filler used in composing the adhesive mixture.

In mixing the resin and filler, it should be kept in mind that not only is viscosity controlled by the actual ratio of resin to filler used, but also the cure time. Thus, a low ratio, for instance, a 1:1 ethyl cyanoacrylate to silane-treated amorphous silica ratio by weight will yield a low viscosity adhesive with a long cure time. A high ratio, say 1:4 by weight of the above ingredients, will yield a high viscosity adhesive with a short cure time.

The optimum mix of ingredients found is a 1:2 ratio of resin to filler. This mix provides a sufficiently viscous adhesive as will not run off the tooth when applied, and yet is not viscous as will entrain air pockets at the mount/bracket interface and weaken the bond. Further, such a mixture (1:2) allows a long enough cure time to give the orthodontist sufficient time to correctly position the mount/bracket structure on the tooth without causing a curing time that would raise the possibility of the adhesive setting in a maladjusted position because of the difficulty of holding the mount/bracket structure correctly over a long period of time. In practice, formulation will be accomplished through the use of a drop-wise fluid dispenser for measuring the cyanoacrylate, and a measuring spoon for the filler. While measurements are described herein in units of weight, these will be converted into more convenient volume measurements for use in the orthodontist's office.

Thus, the curing time can be varied from as great as fifteen minutes to as little as fifteen seconds, at room temperature. Changes in formulation such as different fillers, particle size of the filler, the particular silane used in treating the filler, resins (C=1 to 12), resin viscosity, or the mixing ratio will influence the curing time and consistency of the adhesive used.

A preferred adhesive mixture having optimum properties, such as reasonable pot life and consistency, comprises 1:2 ethyl cyanoacrylate resin and silica mixture. The silica in the mixture has been treated with silanes as in mixture V to render it hydrophobic.

Generally the adhesive should require a room temperature cure of two to four minutes to allow sufficient time to prepare the adhesive and position the mount/bracket structure. This cure time can be accelerated by the application of controlled heat input from an external source. In this manner, an experienced orthodontist can place the mount/bracket structure on the tooth in a correct position and firmly secure the structure in 30 seconds or less with the use of external heat. By such a procedure, the time necessary for an orthodontist to direct bond mount/bracket structures to teeth can be reduced. More precise mount/bracket placements are possible as a result of the decreased time necessary for the final setting of the adhesive.

As a result of the combination of the pretreatment with stannous fluoride and the hydrophobic filler material in the adhesive, the necessity for prophylactic treatment while the mount/bracket structures are on the teeth is greatly reduced as the possibility of caries development on the tooth surface around and beneath the bracket mount is greatly reduced. In effect, there is provided a substantially waterproof bond about the periphery of the mount/bracket interface with the tooth surface. Thus the tooth surface which is in contact with the adhesive is initially protected by the pretreatment with stannous fluoride and subsequent development of caries on that tooth surface is prevented by the substantially waterproof bond. In this manner the integrity of the bond is assured over the length of time in which the orthodontic treatment using the mount/bracket structure is often in place, which is up to 24 months or longer.

Removal of the mount/bracket structure is easily effected and allows the tooth surface at the site of the interface with the mount/bracket structure to be restored to its original state with normal dental prophylactic procedures. A solvent such as dimethylformamide is applied to the periphery of the mount/bracket's interface with the tooth surface to solubilize the cyanoacrylate resin. Concurrent application of moderate mechanical force to the bracket and moderate heat input may be used to assist the solvation of the adhesive. When the adhesive releases its grip on the mount/bracket structure, allowing it to be removed from the tooth surface, the remnants of the adhesive that remain on the tooth may be removed by continued swabbing of the tooth with the solvent in moderate amounts. Final cleansing of the tooth surface may be accomplished by normal dental prophylactic procedures. There is no abrading of the tooth surface in removing the adhesive from the tooth, nor are there etched surfaces, providing pits in the tooth surface in which the adhesive residue may be lodged. The tooth may be completely restored to its original condition with a gentle swabbing technique.

As shown in FIG. 3, the mount/bracket system of securing the arch wire 35 to the teeth for the corrective treatment may be eliminated through the use of the direct bonding technique by embedding the arch wire 35 directly into the adhesive 30. In this embodiment the arch wire should be of a nature which has a memory and will assume a predetermined shape on the application of heat. The pretreatment and mixing of the adhesive are carried out as described above. The adhesive mixture 30 is placed on the tooth over the pretreated area of the tooth surface at a location on the tooth where contact will be made with the arch wire 35. The adhesive should be placed on the tooth surface in such a thickness as will equal or exceed the diameter of the arch wire 35. The arch wire 35 is then secured across the teeth in the desired position for the corrective procedure and embedded into the adhesive. The adhesive is then fully cured in a controlled manner, either at room temperature or with the application of heat as described above. With this application of heat, the arch wire will assume its predetermined shape and thus apply the desired stress on the tooth. In the elimination of the mount/bracket structure it becomes important that the color of the adhesive is carefully matched to the color of the tooth surface onto which it is being applied. Thus, upon careful application of the adhesive and, except upon close examination of the teeth, all that will be visible to the casual observer will be the arch wire 35 running across the teeth. This procedure represents a great aesthetic advantage over previous banding methods of securing the mount/bracket structure to the tooth surface.

The method and composition of the subject invention is ideally suited for use as a dental restorative as shown in FIG. 4. The tooth may develop newly-exposed tooth surfaces as a result of the removal of caries, chipped teeth and the like. The newly-exposed surface is pretreated with the stannous fluoride solution as described above, the adhesive is mixed to achieve the desired consistency and color and applied to the pretreated tooth surface and smoothed down to simulate the tooth outline prior to development of the newly-exposed tooth surface.

In addition, the method and composition of the subject invention may be used in securing dental crowns and bridgework in the desired positions. A further application is the sealing of pits and fissures on the tooth surfaces. These pits and fissures may become the source of caries development as they tend to trap food particles and other sources of damaging bacteria. Therefore unless these pits and fissures on the tooth surfaces are sealed as with the subject inventive method and composition, the incidence of caries will increase. In the above-mentioned applications and in other applications, the strength of the bond interface with the tooth surface, the high durability of the adhesive with the oral environment, and the anticavity protection afforded to the tooth by the treatment all combine to offer an advantageous dental composition for the repair of teeth.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:
1. The method of securing an orthodontic fixture to a tooth surface, comprising the steps of:
   (a) cleaning said tooth surface of extraneous foreign matter,
   (b) swabbing said tooth surface with a stannous fluoride solution and letting said solution remain on said tooth surface for approximately 120 seconds to prepare said tooth surface for the application of an adhesive by providing a bridging means on said tooth surface,
   (c) rinsing excess stannous fluoride solution from said tooth surface, leaving said bridging means on said tooth surface,
   (d) drying said tooth surface,
   (e) combining a cyanoacrylate resin and a hydryphobic filler powder in a ratio for providing a desired cure time and viscosity,
   (f) mixing said resin and said powder to form a homogenous adhesive,
   (g) placing said adhesive on a side of said orthodontic fixture for engaging said tooth surface with said bridging means thereon,
   (h) placing said side of said orthodontic fixture with said adhesive in a desired position on said tooth surface,
   (i) applying pressure to said orthodontic fixture against said tooth surface, and retaining said orthodontic fixture in said desired position until said adhesive interacts with said bridging means and cures,
said fixture thereby being secured to said tooth surface in said desired position by a strong bond at a tooth surface interface with said fixture including said adhesive and said bridging means and capable of enduring long periods of time in an oral environment.

2. The method of claim 1 wherein said resin and said powder are combined in ratios of one part by weight of said resin with one part by weight of said powder to one part by weight of said resin with four parts by weight of said powder.

3. The method of claim 1 wherein said heat is applied from an external source to said orthodontic fixtures and said tooth surface to accelerate the curing of said adhesive.

4. The method of claim 1 further including the step of removing said orthodontic fixture from said tooth surface by swabbing a solvent about said tooth surface interface with said fixture to solvate said adhesive.

5. The method of claim 1 further including the step of adding an inorganic colorant to match the color of the adhesive composition with the color of the tooth.

6. The method of claim 1 wherein said adhesive is formed in the ratio of from approximately 1 part by weight of said resin for every 1 part by weight of said powder to approximately 1 part by weight of said resin for every 4 parts by weight of said powder.

7. The method of claim 1 wherein said adhesive is formed in the ratio of 1 part by weight of said resin to 2 parts by weight of said powder.

8. The method of claim 1 wherein said powder is silane treated.

9. The method of claim 1 wherein said powder is treated with a combination of silanes selected from the group comprising:
Vinyl-tris (beta-methoxyethoxy) silane,
gamma-Methacryloxypropyltrimethoxysilane,
beta-(3,4-Epoxycyclohexyl) ethyltrimethoxysilane,
gamma-Glycidoxypropyltrimethoxysilane,
gamma-Mercaptopropyltrimethoxysilane,
gamma-Aminopropyltriethoxysilane,
N-beta-(aminoethyl)-gamma-aminopropyltriethoxysilane, and
Styryl amine functional silane.

10. The method of claim 1 wherein said cyanoacrylate resin is a liquid ester cyanoacrylate of the formula $$CH_2=\underset{CN}{C}-COOR$$

where R is a hydrocarbon or fluorocarbon of from 1-12 atoms.

11. The method of claim 1 wherein said cyanoacrylate resin is ethyl cyanoacrylate.

12. The method of claim 1 wherein said powder is selected from the group of: calcium carbonate, aluminum silicates, magnesium silicates, alumnia, silica, Kaolinite, Bentonite, and Montmorilonite.

13. The method of claim 1 wherein an inorganic colorant is added to match the color of the adhesive composition with the color of the tooth.

14. A method of repairing an exposed rough tooth surface, such as occurs in the removal of caries, an injury to a tooth and the like and leaving a reconstructed surface on said tooth, comprising the steps of:
(a) cleaning said exposed tooth surface of extraneous foreign matter by conventional prophylactic procedures,
(b) swabbing said exposed tooth surface with a stannous fluoride solution, letting said solution remain on said tooth surface approximately 120 seconds to prepare said tooth surface for the application of an adhesive by providing a bridging means on said tooth surface,
(c) removing the excess of said stannous fluoride from said exposed tooth surface with a rinse of water, leaving said bridging means on said tooth surface,
(d) combining a homogenous mixture of a cyanoacrylate resin and a hydrophobic inorganic filler, in a ratio providing a desired cure time and viscosity in said mixture,
(e) placing a portion of said mixture over said exposed rough tooth surface for contact with said bridging means and smoothing said mixture to approximately the original tooth surface contour, and
(f) letting said mixture interact with said bridging means and tooth surface and cure;
whereby a reconstructed surface is formed on the tooth, said reconstructed surface comprising said mixture and said bridging means adhering to said tooth surface, said reconstructed surface having good endurance qualities in the oral environment of the mouth, being resistant to wear and to deterioration of the restorative surface.

15. The method of claim 14 wherein an inorganic colorant is added to said adhesive for adjusting the color of said adhesive to match the color of said tooth surface.

* * * * *